(12) United States Patent
Burgess et al.

(10) Patent No.: US 11,628,135 B2
(45) Date of Patent: Apr. 18, 2023

(54) WATER-BASED NAIL-TREATMENT COMPOSITION

(71) Applicant: Coty Inc., New York, NY (US)

(72) Inventors: Tamara L. Burgess, Morris Plains, NJ (US); Yelena Loginova, Bronx, NY (US); Beate Boutwell, Sparta, NJ (US)

(73) Assignee: COTY, INC., New York, NY (US)

( * ) Notice: Subject to any disclaimer, the term of this patent is extended or adjusted under 35 U.S.C. 154(b) by 39 days.

(21) Appl. No.: 16/479,090

(22) PCT Filed: Feb. 23, 2018

(86) PCT No.: PCT/US2018/019469
§ 371 (c)(1),
(2) Date: Jul. 18, 2019

(87) PCT Pub. No.: WO2018/156927
PCT Pub. Date: Aug. 30, 2018

(65) Prior Publication Data
US 2019/0388330 A1   Dec. 26, 2019

Related U.S. Application Data

(60) Provisional application No. 62/464,172, filed on Feb. 27, 2017.

(51) Int. Cl.
| | | |
|---|---|---|
| *A61K 8/81* | (2006.01) | |
| *A61K 8/9794* | (2017.01) | |
| *A61K 8/9789* | (2017.01) | |
| *A61K 8/36* | (2006.01) | |
| *A61K 8/40* | (2006.01) | |
| *A61K 8/86* | (2006.01) | |
| *A61K 8/92* | (2006.01) | |
| *A61K 8/97* | (2017.01) | |
| *A61Q 3/02* | (2006.01) | |

(52) U.S. Cl.
CPC ........... *A61K 8/8147* (2013.01); *A61K 8/36* (2013.01); *A61K 8/40* (2013.01); *A61K 8/86* (2013.01); *A61K 8/922* (2013.01); *A61K 8/97* (2013.01); *A61K 8/9789* (2017.08); *A61K 8/9794* (2017.08); *A61Q 3/02* (2013.01)

(58) Field of Classification Search
None
See application file for complete search history.

(56) References Cited

U.S. PATENT DOCUMENTS

| | | | |
|---|---|---|---|
| 5,830,443 A | 11/1998 | Lee | |
| 6,555,117 B2 | 4/2003 | Midha et al. | |
| 6,939,551 B2 | 9/2005 | Amato et al. | |
| 9,017,704 B2 | 4/2015 | Blin et al. | |
| 2004/0013622 A1* | 1/2004 | Godbout | A61Q 3/02 424/195.17 |
| 2007/0196325 A1* | 8/2007 | Zhang | A61K 31/522 424/78.07 |
| 2007/0286838 A1* | 12/2007 | Axelrod | A61K 36/185 424/74 |
| 2009/0317432 A1 | 12/2009 | Kergosien | |
| 2014/0335167 A1 | 11/2014 | Panandiker et al. | |
| 2016/0088919 A1 | 3/2016 | Oohashi | |

FOREIGN PATENT DOCUMENTS

| | | |
|---|---|---|
| CA | 2428735 A1 | 11/2003 |
| JP | 2014224082 A | 12/2014 |
| WO | WO-02062894 A1 | 8/2002 |
| WO | WO-2014028021 A1 | 2/2014 |
| WO | WO-2015061485 A1 | 4/2015 |
| WO | WO-2015165897 A1 | 11/2015 |
| WO | WO-2016099877 A1 | 6/2016 |
| WO | WO-2018156927 A1 | 8/2018 |

OTHER PUBLICATIONS

"International Application Serial No. PCT/US2018/019469, International Search Report dated Apr. 30, 2018", 2 pgs.
"International Application Serial No. PCT/US2018/019469, Written Opinion dated Apr. 30, 2018", 6 pgs.
"International Application Serial No. PCT/US2018/019469, International Preliminary Report on Patentability dated Sep. 6, 2019", 8 pgs.
"European Application Serial No. 18756870.4, Extended European Search Report dated Dec. 16, 2020", 8 pgs.
"Pump Up the Colour Mascara", Database GNPD [Online] MINTEL, Database accession No. 243139, (Dec. 10, 2003).
"European Application Serial No. 18756870.4, Communication Pursuant to Article 94(3) EPC dated Sep. 30, 2022", 4 pgs.

* cited by examiner

*Primary Examiner* — David J Blanchard
*Assistant Examiner* — Sarah J Chickos
(74) *Attorney, Agent, or Firm* — Schwegman Lundberg & Woessner, P.A.

(57) ABSTRACT

Various embodiments disclosed relate to water-based nail-treatment compositions including a first film-forming copolymer that is a copolymer of a ($C_1$-$C_5$)alkyl ester of methacrylic acid, of a ($C_1$-$C_5$)alkyl ester of acrylic acid, or a combination thereof, and of methacrylic acid. The nail-treatment compositions also include a second film-forming copolymer that is a copolymer of isophorone diisocyanate, a poly(($C_2$-$C_3$)alkylene oxide), and 2,2-bis(methylol)propionic acid. Methods of using the nail-treatment compositions and cured products of the same are also provided. A cured product of the nail-treatment composition can be monolithically peelable from the nail.

20 Claims, 3 Drawing Sheets

WATER-BASED NAIL-TREATMENT COMPOSITION

CROSS-REFERENCE TO RELATED APPLICATION

This application is a U.S. National Stage Filing under 35 U.S.C. 371 from International Application No. PCT/US2018/019469, filed on Feb. 23, 2018, and published as WO2018/156927 on Aug. 30, 2018, which application claims the benefit of priority to U.S. Provisional Patent Application Ser. No. 62/464,172 entitled "WATER-BASED NAIL-TREATMENT COMPOSITION," filed Feb. 27, 2017, both of which are incorporated herein in their entirety by reference.

BACKGROUND

Volatile organic solvents in nail polish can be toxic, can cause unpleasant olfactory sensations for the user, and can dry out the nail. Conventional water-based nail polish suffers from difficult removal from the nail, including when using acetone nail polish remover. Excessive chipping can make water-based nail polish less desirable to wear.

SUMMARY OF THE INVENTION

In various embodiments, the present invention provides a water-based nail-treatment composition. The water-based nail-treatment composition includes a first film-forming copolymer that is a copolymer of a ($C_1$-$C_5$)alkyl ester of methacrylic acid, of a ($C_1$-$C_5$)alkyl ester of acrylic acid, or a combination thereof, and of methacrylic acid. The water-based nail-treatment composition also includes a second film-forming copolymer that is a copolymer of isophorone diisocyanate, a poly(($C_2$-$C_3$)alkylene oxide), and 2,2-bis(methylol)propionic acid.

In various embodiments, the present invention provides a water-based nail-treatment composition including a first film-forming copolymer that is about 5 wt % to about 90 wt % of the nail treatment composition and that is a copolymer of methacrylic acid, butyl acrylate, and methyl methacrylate. The water-based nail-treatment composition includes a second film-forming copolymer that is about 1 wt % to about 95 wt % of the nail-treatment composition and that is a copolymer of isophorone diisocyanate, polypropylene glycol-17, and 2,2-bis(methylol)propionic acid. The nail-treatment composition is substantially free of nitrocellulose. A cured nail coating formed from the nail-treatment composition is monolithically peelable from the nail.

Various embodiments of the present invention provide a cured product of the nail-treatment composition.

In various embodiments, the present invention provides a nail-treatment composition including a biomimetic composition. The biomimetic composition includes an oil-based portion including two or more of green coffee oil, coconut oil, and Abyssinian oil. The biomimetic composition optionally includes a water-based portion including garlic extract, horsetail extract, marshmallow extract, or a combination thereof.

In various embodiments, the present invention provides a method of using the nail-treatment composition. The method includes applying the nail-treatment composition to a nail surface. The method also includes allowing the nail-treatment composition to cure on the nail surface to form a cured product of the nail-treatment composition.

The water-based nail-treatment composition of the present invention provides certain advantages over other nail-treatment compositions, cured products thereof, and methods of using the same. For example, in various embodiments, a cured product of the nail-treatment composition of the present invention can be more easily removable, such as using conventional acetone nail polish removers or via other means, as compared to cured products of other nail-treatment compositions. In various embodiments, a cured product of the nail-treatment composition of the present invention can be more easily peelable, such as more easily monolithically peelable, from a nail, as compared to cured products of other nail-treatment compositions. In various embodiments, a cured product of the nail-treatment composition of the present invention can provide for longer wear times (e.g., with less or no chipping or other degradation of appearance) than cured products of other nail-treatment compositions.

In various embodiments, a cured product of the nail-treatment composition of the present invention can better protect visual effects delivered by use of effect pigment in other layers, such as after volatile organic solvent-based polish is applied on top of the effect pigment, as compared to cured products of other nail-treatment compositions. For example, effect pigments which provide a chrome mirror finish can become dull when a solvent-based top coat is applied on top of the chrome finish. In various embodiments, when the nail-treatment composition of the present invention is applied over the chrome effect, the mirror finish is maintained; further, after the nail-treatment composition has cured (e.g., dried), a solvent top coat can then be applied without affecting the chrome effect mirror finish. In another example, typically glitter effect pigments can be difficult remove from the nail. If removal is not possible with acetone nail polish remover, the remaining glitter pigment can be buffed off with a nail file. In various embodiments, the nail-treatment composition can be used as a basecoat to make the glitter pigment easier to remove with acetone or by peeling.

In various embodiments, the nail-treatment composition of the present invention can provide healthier nails as compared to use with other nail-treatment compositions, such as nails that are less dry, less brittle, and that have a healthier appearance. In various embodiments, the nail-treatment composition of the present invention can provide a higher shine and a higher impact color (e.g., in embodiments including one or more pigments), as compared to use with other nail-treatment compositions.

In various embodiments, the nail-treatment composition of the present invention can have broader temperature stability as compared to other nail-treatment compositions. For example, various embodiments of the nail-treatment composition remains useable and components thereof do not settle out of the composition, such as after 5 or more freeze-thaw cycles (e.g., about 1 to about 20 or more freeze-thaw cycles, or about 1, or less than, equal to, or greater than 2, 3, 4, 5, 6, 7, 8, 9, 10, 12, 14, 16, 18, or about 20 or more). In various embodiments, the nail-treatment composition of the present invention can have less or substantially no nitrocellulose, volatile organic solvents, plasticizers, or a combination thereof, such as compared to other nail-treatment compositions.

BRIEF DESCRIPTION OF THE FIGURES

The drawings illustrate generally, by way of example, but not by way of limitation, various embodiments of the present invention.

DETAILED DESCRIPTION OF THE INVENTION

Reference will now be made in detail to certain embodiments of the disclosed subject matter. While the disclosed subject matter will be described in conjunction with the enumerated claims, it will be understood that the exemplified subject matter is not intended to limit the claims to the disclosed subject matter.

Throughout this document, values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. The statement "at least one of A and B" or "at least one of A or B" has the same meaning as "A, B, or A and B." In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section.

In the methods described herein, the acts can be carried out in any order without departing from the principles of the invention, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range, and includes the exact stated value or range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more, or 100%. The term "substantially free of" as used herein can mean having none or having a trivial amount of, such that the amount of material present does not affect the material properties of the composition including the material, such that the composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less. The term "substantially free of" can mean having a trivial amount of, such that a composition is about 0 wt % to about 5 wt % of the material, or about 0 wt % to about 1 wt %, or about 5 wt % or less, or less than, equal to, or greater than about 4.5 wt %, 4, 3.5, 3, 2.5, 2, 1.5, 1, 0.9, 0.8, 0.7, 0.6, 0.5, 0.4, 0.3, 0.2, 0.1, 0.01, or about 0.001 wt % or less, or about 0 wt %.

The term "hydrocarbon" or "hydrocarbyl" as used herein refers to a molecule or functional group that includes carbon and hydrogen atoms. The term can also refer to a molecule or functional group that normally includes both carbon and hydrogen atoms but wherein all the hydrogen atoms are substituted with other functional groups.

As used herein, the term "hydrocarbyl" refers to a functional group derived from a straight chain, branched, or cyclic hydrocarbon, and can be alkyl, alkenyl, alkynyl, aryl, cycloalkyl, acyl, or any combination thereof. Hydrocarbyl groups can be shown as $(C_a\text{-}C_b)$hydrocarbyl, wherein a and b are integers and mean having any of a to b number of carbon atoms. For example, $(C_1\text{-}C_4)$hydrocarbyl means the hydrocarbyl group can be methyl $(C_1)$, ethyl $(C_2)$, propyl $(C_3)$, or butyl $(C_4)$, and $(C_o\text{-}C_b)$hydrocarbyl means in certain embodiments there is no hydrocarbyl group.

As used herein, the term "polymer" refers to a molecule having at least one repeating unit and can include copolymers.

The term "cure" as used herein refers to exposing to radiation in any form, heating, or allowing to undergo a physical or chemical reaction that results in hardening or an increase in viscosity. The nail-treatment composition of the present invention can be cured by allowing the nail-treatment composition to dry on a nail, which causes it to harden.

Water-Based Nail-Treatment Composition.

In various embodiments, the present invention provides a water-based nail-treatment composition. The nail-treatment composition can include a first film-forming copolymer that is a copolymer of a $(C_1\text{-}C_5)$alkyl ester of methacrylic acid, of a $(C_1\text{-}C_5)$alkyl ester of acrylic acid, or a combination thereof, and of methacrylic acid. The nail-treatment composition can include a second film-forming copolymer that is a copolymer of isophorone diisocyanate, a poly(($C_2\text{-}C_3$) alkylene oxide), and 2,2-bis(methylol)propionic acid.

The nail-treatment composition can be used as any suitable coating in a nail-treatment method. The nail-treatment composition can be a basecoat (e.g., can be applied directly to the nail without intervening layers). The nail-treatment composition can be used as a basecoat with or without pigments. The nail-treatment composition can be used as a basecoat with or without layers placed on top of a cured product of the nail-treatment composition. In other embodiments, the nail-treatment composition can be used as a secondary coat or topcoat (e.g., is placed on top of other cured layers of nail-treatment composition). The nail-treatment composition can be an enamel.

In various embodiments, a cured nail coating formed from the nail-treatment composition can be monolithically peelable from the nail, such that the cured coating can be peeled from the nail in a single continuous film. The cured product of the nail-treatment composition can be a long wear composition and remain wearable for any suitable period of time, such as for about 1-30 days, 1-14 days, or 1-5 days, or 1-3 days, or about 1 day or less, or less than, equal to, or greater than about 2 days, 3, 4, 5, 6, 7, 8, 9, 10, 11, 12, 13, 14, 15, 16, 17, 18, 19, 20, 25, or about 30 or more days. The cured product can be removed by peeling and lifting the enamel layer as one continuous film. Users can use one or more fingernails to pull the cured product away from the cuticle or sidewall of the nail. When the cured product includes a tab or other protrusion, a user can grab the protrusion and peel the coating off as a single piece.

In various embodiments, the nail-treatment composition can include a first film-forming copolymer that is a copolymer of a ($C_1$-$C_5$)alkyl ester of methacrylic acid, of a ($C_1$-$C_5$)alkyl ester of acrylic acid, or a combination thereof, and of methacrylic acid. The first film-forming copolymer can be a copolymer of methacrylic acid, butyl acrylate, and methyl methacrylate. The nail-treatment composition can include one first film-forming copolymer or more than one first-film-forming copolymer. The one or more first film-forming copolymers can be any suitable proportion of the nail-treatment composition, such as about 1 wt % to about 90 wt % of the nail-treatment composition, about 30 wt % to about 65 wt %, about 40 wt % to about 55 wt %, or about 42 wt % to about 53 wt %, or about 1 wt % or less, or less than, equal to, or greater than about 2 wt %, 3, 4, 5, 6, 7, 8, 9, 10, 12, 14, 16, 18, 20, 22, 24, 26, 28, 30, 32, 34, 36, 38, 40, 45, 50, 52, 54, 56, 58, 60, 62, 64, 66, 68, 70, 72, 74, 76, 78, 80, 82, 84, 86, 88, 90, 91, 92, 93, 94, or about 95 wt % or more. An example of a suitable commercial product including a suitable first film-forming copolymer is Daitosol 3000SPLN-PE1.

In various embodiments, the nail-treatment composition can include a second film-forming copolymer that is a copolymer of isophorone diisocyanate, a poly(($C_2$-$C_3$)alkylene oxide), and 2,2-bis(methylol)propionic acid. The polyoxy($C_2$-$C_3$)alkylene can be a poly(propylene oxide). The polyoxy($C_2$-$C_3$)alkylene can be a poly(propylene oxide) having a degree of polymerization of about 17. The second film-forming copolymer can be a copolymer is polypropylene glycol-17, isophorone diisocyanate, and 2,2-bis(methylol)propionic acid. The nail-treatment composition can include one second film-forming polymer or more than one second film-forming polymer. The one or more second film-forming polymers can be any suitable proportion of the nail-treatment composition, such as about 1 wt % to about 95 wt % of the nail-treatment composition, about 5 wt % to about 95 wt %, or about 5 wt % to about 20 wt %, or about 10 wt % to about 16 wt %, or about 1 wt % or less, or less than, equal to, or greater than about 2 wt %, 3, 4, 5, 6, 7, 8, 9, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 91, 92, 93, 94, or about 95 wt % or more. An example of a suitable commercial product including a suitable second film-forming copolymer is Avalure™ UR 450.

In various embodiments, the nail-treatment composition can include one or more thickeners. The thickener can be an associative thickener, a non-associative thickener, or a combination thereof (e.g., an associative and non-associative hybrid thickener). The thicknener can be one or more polymer or copolymer including repeating units formed from one or more of acrylic acid and of methacrylic acid or a ($C_1$-$C_5$)alkyl ester thereof. The polymer or copolymer can be optionally crosslinked. The thickener can be a copolymer of steareth-20 methacrylate (e.g., a steareth-20 ester of methacrylic acid, wherein steareth-20 is a PG 20 stearic acid ether) or steareth-20 itaconate and one or more of acrylic acid and of methacrylic acid or a ($C_1$-$C_5$)alkyl ester thereof, wherein the copolymer is crosslinked with an allyl ether of pentaerythritol, an allyl ether of trimethylolpropane, or a combination thereof. The one or more thickeners can be any suitable proportion of the nail-treatment composition, such as about 0.001 wt % to about 10 wt % of the nail-treatment composition, or about 0.05 wt % to about 2.0 wt %, or less than, equal to, or greater than about 0.001 wt %, 0.005, 0.01, 0.05, 0.1, 0.5, 1, 1.5, 2, 2.5, 3, 3.5, 4, 4.5, 5, 6, 7, 8, 9, or about 10 wt % or more. Examples of commercial products including suitable thickeners include Aculyn™ 88, Aculyn™ 22, Aculyn™ 33, and Structure® 2001.

In various embodiments, water can be any suitable proportion of the water-based nail-treatment composition, such as about 5 wt % to about 95 wt % of the nail-treatment composition, or about 50 wt % to about 70 wt % of the nail-treatment composition, or 5 wt % or less, or less than, equal to, or greater than about 6 wt %, 7, 8, 9, 10, 12, 14, 16, 18, 20, 22, 24, 26, 28, 30, 35, 40, 45, 50, 55, 60, 65, 70, 75, 80, 85, 90, or about 95 wt % or more.

In various embodiments, the nail-treatment composition can optionally include at least one coalescing agent. Suitable coalescing agents can include, for example, glycerol ethers, glycerol ether esters, ester alcohols, and branched or linear ($C_1$-$C_6$)alkyl acetates. For example, suitable ($C_1$-$C_6$)alkyl acetates include methyl acetate, ethyl acetate, propyl acetate, butyl acetate, pentyl acetate, or hexyl acetate, or mixtures thereof. Coalescing agents can reduce the $T_g$ (glass transition temperature) of the nail-treatment compositions described herein, allowing for more efficient film formation. Nail-treatment compositions that include at least one coalescing agent are not peelable. The coalescing agent also slowly evaporates after the water has substantially evaporated from the nail-treatment composition, thereby increasing the $T_g$ and contributing to the improved properties of the nail coating described herein, including improved nail hardness.

It was unexpectedly discovered that using less than about 5 wt % of a coalescing agent in the nail-treatment compositions described herein results in cured products of the nail-treatment composition that have longer wear times. At amounts greater than about 5 wt %, the coalescing agent acts as a volatile organic solvent and results in an incompatible system that does not provide the beneficial long wear properties obtained when less than about 5 wt % of the coalescing agent is used. Without being bound by theory, it is believed that using greater than about 5 wt % of a coalescing agent results in an incompatibility with the second film-forming copolymer described herein. The coalescing agent can be less than about 5 wt % of the nail-treatment composition, or about 0.01 to about 5 wt %, about 0.1 to about 4 wt %, about 0.25 to about 3.5 wt %, about 0.5 to about 3 wt %, or about 0.75 to about 2.5 wt % of the nail-treatment composition, or less than, equal to, or greater than about 4, 3.5, 3, 2.5, 2, 1.9, 1.8, 1.7, 1.6, 1.5, 1.4, 1.3, 1.2, 1.1, 1.0, 0.9, 0.8, 0.7, 0.6, 0.5, 0.4, 0.3, 0.2, 0.1, 0.05, 0.025, or 0.01 wt %. In various embodiments, the coalescing agent is less than about 5 wt % butyl acetate.

In various embodiments, the nail-treatment composition can include one or more colorants. Alternatively, in various embodiments, the nail-treatment composition can be substantially free of colorants.

In various embodiments, the nail-treatment composition can be substantially free of nitrocellulose, nitrocellulose derivatives, or a combination thereof. In various embodiments, the nail-treatment composition can be substantially free of volatile organic solvents such as acetone, ethyl acetate in amounts of greater than about 5 wt % of the nail-treatment composition, or a combination thereof. In various embodiments, the nail-treatment composition can be substantially free of phthalates. In various embodiments, the nail-treatment composition can be substantially free of plasticizers, due, for example, to the use of the first and second film-forming polymers.

In various embodiments, the nail-treatment composition can include or be substantially free of any of a defoamer, an adhesion promoter, a film-forming polymer, a photoinitiator, a filler, a rheology modifier, a thixotropic agent, a plasticizer, an oil, a UV absorber, a UV stabilizing agent, a surfactant, a dispersant, or a combination thereof.

Biomimetic Composition.

Nail beauty is an important attribute of the overall attractiveness of hands, and nail health depends at least in part on the oil/water balance in human skin and the integumentary system. The role of oils in nails is therefore important since nails do not have sebaceous glands. The combination of oil and water as a cement can hold the nail plate layers together supporting its natural flexibility. The dehydration of splitting or peeling nails can be restored by using at least one effective cuticle and/or nail oil, thereby improving or maintaining nail health.

In various embodiments, the nail-treatment composition can further include a biomimetic composition. The biomimetic composition can be deposited onto a nail and subsequently becomes sealed when the composition cures as water naturally evaporates, leaving behind a durable protective coat (e.g., basecoat) that can aid in returning the nail back to health within about 14 days after application of a nail-treatment composition containing a biomimetic composition as described herein. After removal of the nail-treatment composition, nails can appear stronger, more moisturized, and brighter, with less prominent and defined nail ridges. The biomimetic composition can be any suitable proportion of the nail-treatment composition, such as about 0.001 wt % to about 50 wt % of the nail-treatment composition, or about 0.001 wt % or less, or less than, equal to, or greater than about 0.005 wt %, 0.01, 0.05, 0.1, 0.5, 1, 2, 3, 4, 5, 6, 7, 8, 9, 10, 12, 14, 16, 18, 20, 25, 30, 35, 40, 45 wt %, or about 50 wt % or more.

The biomimetic composition can include an oil-based portion, which can be about 0.01 wt % to about 100 wt % of the biomimetic composition, or about 0.01 wt % or less, or less than, equal to, or greater than about 0.05 wt %, 0.1, 0.5, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 96, 97, 98, 99, 99.9, or about 99.99 wt % or more. The oil-based portion can include one or more natural oils, or two or more natural oils, such as Abyssinian oil, coconut oil, green coffee oil, or a combination thereof.

In various embodiments, an effective oil combination that improves appearance of human nails and the cuticle can contain green coffee oil, coconut oil, Abyssinian oil, and combinations thereof. Green coffee oil has high levels of chlorogenic acid, which is a powerful antioxidant, as well as significant amounts of fatty acids and phytosterols. This oil promotes good moisture retention and rapid skin penetration. The antioxidant properties based on the amount of polyphenols exhibited by the green coffee oil is 3 times greater compared to green tea and four greater compared to vitamin C. Green coffee oil supports the moisture balance of the skin, controls itchiness, scaling and dead cell build-up, and stimulates detoxification of the skin, making it useful for nail treatment. Coconut oil contains lauric acid as a main constituent, which is converted in the body into monolaurin. This monoglyceride compound exhibits antiviral, antimicrobial, antiprotozoal and antifungal properties via disrupting the lipid membranes in organisms such as fungus, bacteria and viruses, thereby killing them. Abyssinian oil comes from the seed of a mustard plant native to the Mediterranean regions of Europe and has great resistance to oxidation. Abyssinian oil also has a high percentage of unsaturated C22 fatty acids and is easily absorbed into the epidermal tissue without leaving behind a greasy residue. In hair, Abyssinian oil forms a light lipid layer that softens hair and improves luster without greasiness. Table 1A-1C shows the typical fatty acid esters that are present in various oils.

TABLE 1A

Green coffee oil fatty acid esters, typical wt %.

| C16:0 | Palmitic | 40.0 |
| C18:2 | Linoleic | 38.0 |
| C18:0 | Stearic | 8.0 |
| C18:1 | Oleic | 8.0 |
| C18:3 | Linolenic | 2.0 |
| C22:0 | Behenic | 1.0 |
| C16:1 | Palmitoleic | 0.4 |

TABLE 1B

Abyssinian oil fatty acid esters, typical wt % range.

| C16:0 | Palmitic | 1.0-4.0 |
| C16:1 | Palmitoleic | 0.1-0.5 |
| C18:0 | Stearic | 0.5-2.0 |
| C18:1 | Oleic | 10.0-25.0 |
| C18:2 | Linoleic | 7.0-15.0 |
| C18:3 | Linolenic | 2.0-5.0 |
| C20:0 | Arachidic | 0.5-2.0 |
| C20:1 | Eicosenoic | 2.0-6.0 |
| C20:2 | Eicosadienoic | 0.0-0.5 |
| C22:0 | Behenic | 1.0-3.0 |
| C22:1 | Erucic (cis-13-docosenoic acid) | 50.0-65.0 |
| C24:0 | Lignoceric | 0.0-1.0 |

TABLE 1C

Coconut oil fatty acid esters, typical wt %.

| | | Fatty acids of Coconut Oil (%) |
| --- | --- | --- |
| C6:0 | Caproic | 0.5 |
| C8:0 | Caprylic | 7.8 |
| C10:0 | Capric | 6.7 |
| C12:0 | Lauric | 47.5 |
| C14:0 | Myristic | 18.1 |
| C16:0 | Palmitic | 8.8 |
| C18:0 | Stearic | 2.6 |
| C18:1 | Oleic | 6.2 |
| C18:2 | Linoleic | 1.6 |

Figure 1:
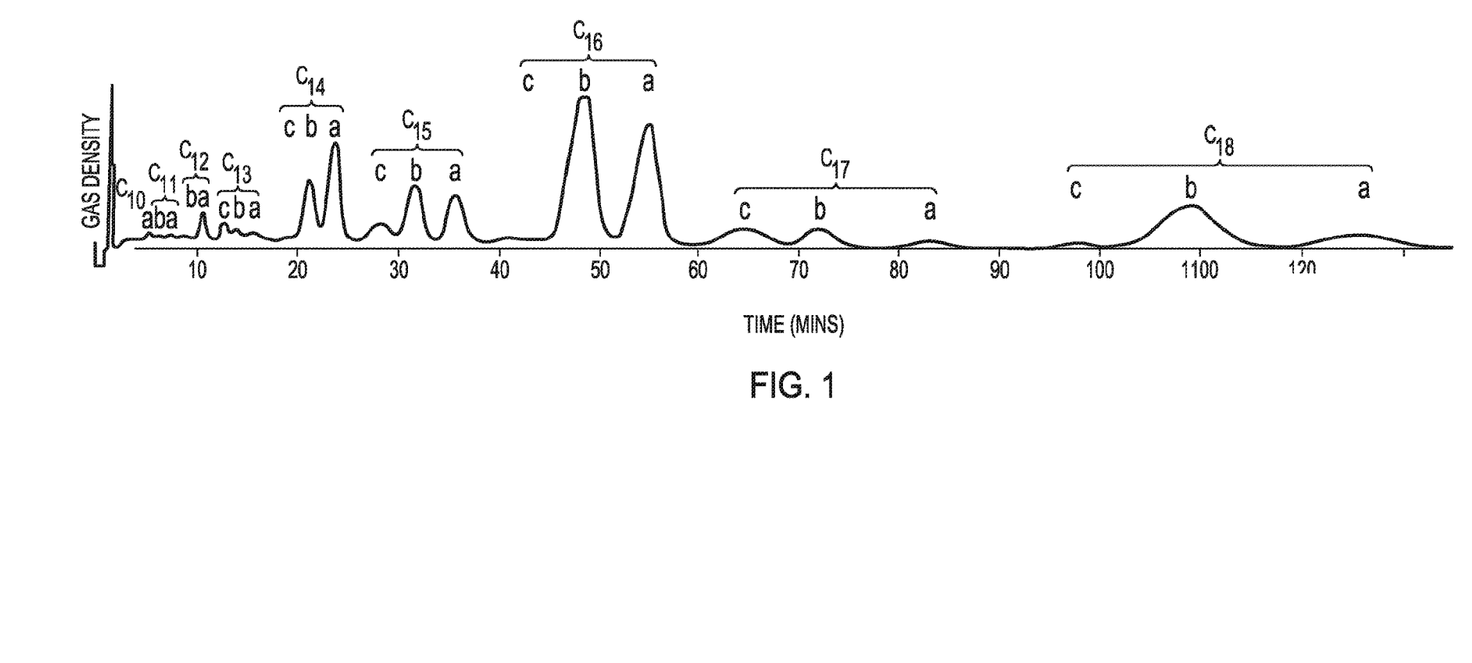
FIG. 1 illustrates a gas chromatograph of the total fatty acids in combination from the back (sebum) of a female human subject.

FIG. 1 illustrates a gas chromatograph of the total fatty acids in combination from the back (sebum) of a female human subject. Table 2 illustrates the main fatty acids in a combination of green coffee oil, Abyssinian oil, and coconut oil, showing that the combination contains C14, C16, and C18 fatty acid esters, corresponding to natural oils as shown in FIG. 1. The correlation between the oil combination and skin lipids can positively affect nails after an application of such composition.

TABLE 2

Main fatty acids of combination of green coffee oil, Abyssinian oil, and coconut oil.

| | |
|---|---|
| C16:0 | Palmitic |
| C18:2 | Linoleic |
| C22:1 | Erucic (cis-13-docosenoic acid) |
| C18:1 | Oleic |
| C12:0 | Lauric |
| C14:0 | Myristic |

The biomimetic composition can include a water-based portion, which can be about 0.01 wt % to about 100 wt % of the biomimetic composition, or about 0.01 wt % or less, or less than, equal to, or greater than about 0.05 wt %, 0.1, 0.5, 1, 2, 3, 4, 5, 6, 7, 8, 9, 10, 12, 14, 16, 18, 20, 25, 30, 35, 40, 45, 50, 55, 60, 65, 70, 75, 80, 85, 90, 95, 96, 97, 98, 99, 99.9, or about 99.99 wt % or more. The water-based portion can include one or more natural extracts, or two or more natural extracts, such as garlic extract, horsetail extract, marshmallow extract, or a combination thereof.

Cured Product of the Nail-Treatment Composition.

In various embodiments, the present invention provides cured product of then nail-treatment composition. The cured product can be any suitable cured product of any embodiment of the nail-treatment composition described herein, and that can be formed using any suitable embodiment of using the nail-treatment composition described herein. In various embodiments, the nail-treatment composition can be cured by allowing it to dry (e.g., allowing water to evaporate from the composition) and harden.

Method of Using the Nail-Treatment Composition.

In various embodiments, the present invention provides a method of using the nail-treatment composition. The method can be any suitable method of using an embodiment of the nail-treatment composition described herein. For example, the method can include applying the nail-treatment composition to a nail surface. The method can include allowing the nail-treatment composition to cure on the nail surface to form a cured product of the nail-treatment composition.

The method can include applying the nail-treatment composition directly to the nail surface without any intervening layers (e.g., as a basecoat) or can include applying the nail-treatment composition to one or more intervening layers (e.g., as a secondary coat or topcoat, such as on top of layer including effect pigments). The method can further include applying one or more additional layers of nail-treatment composition on top of the cured layer, wherein the additional layers of nail-treatment composition are an embodiment of the nail-treatment composition of the present invention or are a different nail-treatment composition (e.g., a volatile solvent-based nail-treatment composition, a UV- or LED-curable nail-treatment composition, or a combination thereof).

In various embodiments, an effect pigment can be added on top of the cured product of the nail-treatment composition. In various embodiments, the nail-treatment composition is applied on top of effect pigments. The cured product of the nail-treatment composition can protect and preserve the effect delivered by the effect pigments, such as from any subsequent layers of nail-treatment compositions (e.g., containing volatile-organic solvents that could disrupt or degrade an unprotected effect pigment). Examples of effect pigments can include aluminum, silver, borosilicate, aluminum calcium sodium silicate, tin oxide, chromium oxide, or a combination thereof.

EXAMPLES

Various embodiments of the present invention can be better understood by reference to the following Examples which are offered by way of illustration. The present invention is not limited to the Examples given herein.

Example 1

Preparation of Samples

Sample 1 and 2 were preparing having the compositions described in Table 2. The term PPG-17/IPDI/DMPA indicates a polyoxypropylene (17), isophorone diisocyanate, and dimethylol propionic acid copolymer.

TABLE 2

Samples 1 and 2.

| Component | Sample 1 | Sample 2 |
|---|---|---|
| Daitosol 3000SPLN-PE1<br>28-32 wt % water<br>67-71 wt % acrylates copolymer<br>CAS 25035-69-2<br>(copolymer of methacrylic acid, butyl acrylate, and methyl methacrylate) | 74.62 wt % | 59.7% |
| Avalure ™ UR 450 water-dispersible film-forming polymer<br>40 wt % PPG-17/IPDI/DMPA copolymer<br>60 wt % water | 24.88 wt % | 39.8 wt % |
| Aculyn ™ 88 thickener/rheology modifier<br>28-30 wt % acrylates/steareth-20 methacrylate crosspolymer<br>70-72 wt % water | 0.5 wt % | 0.5 wt % |

Example 2

Testing of Samples

A lower concentration of less than 15 wt % Avalure™ UR 450 by weight of the base coat made the base coat more difficult for users to peel as a single removed base coat. More than 20 wt % Avalure™ UR 450 by weight of the base coat produced a softer peelable coating with minimal substantivity (e.g., adherence) on the nail.

An Erichsen Pendulum Hardness Tester Model 299/300 was used following ASTM D4366-95/NFT 30-016 to determine the film hardness of Samples 1 and 2 from Example 1, with results shown in Table 3. The films were formed on a 4×6 inch glass plate. Prior to hardness testing, the films were stored for at least 30 minutes in an oven set to 25° C. with a relative humidity of about 20% to about 30%, or were stored for at least 30 minutes in a humidity chamber at 25° C. with a relative humidity of 70-80%. As the film developed over time, Sample 2, having 40 wt % Avalure UR 450, created a softer film that peeled off very easily. After 24 hours, Sample 1, having 25 wt % Avalure UR 450, had a significantly harder film that was more substantive and harder to peel. The film hardness of Sample 2 with 40% Avalure UR 450 continued to increase after 48 hours, which provides evidence that a softer peelable film was achieved. The film hardness of the formula with 25% Avalure UR 450 did not continue to increase after 48 hours, which provides evidence that the film is harder, yet still peelable.

TABLE 3

Erichsen Hardness of films formed from
Samples 1 and 2 after 24 and 48 hours.

| RH | Sample 1 | | Sample 2 | |
| --- | --- | --- | --- | --- |
| | 20-30% | 70-85% | 20-30% | 70-85% |
| 24 h | 131 | 51 | 80 | 38 |
| 48 h | 133 | 51 | 100 | 41 |

"RH" stands for relative humidity.

Figure 2A:
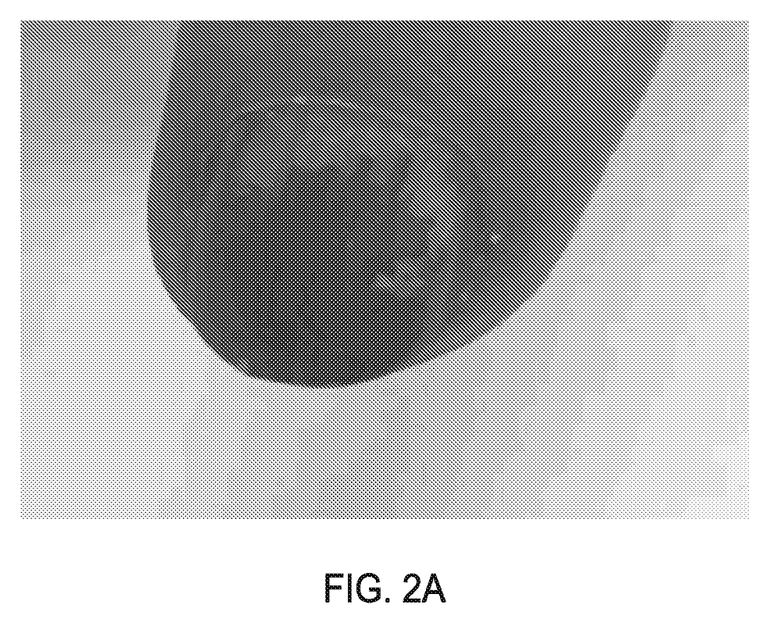
FIG. 2A and FIG. 2B illustrate attempted peeling of a comparative nail treatment composition.
Figure 2B:
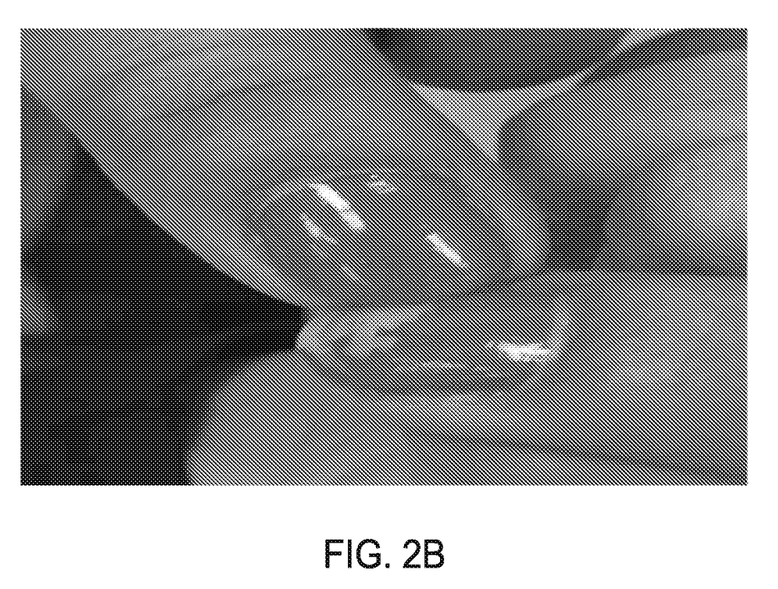
Figure 3A:
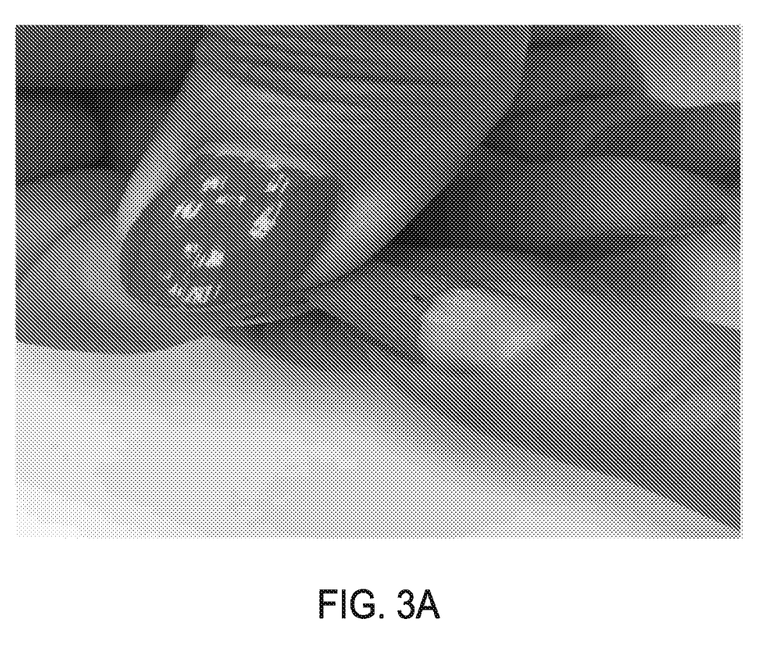
FIG. 3A and FIG. 3B illustrate peeling of a cured coating formed from a water-based nail-treatment composition of the present invention, in accordance with various embodiments.
Figure 3B:
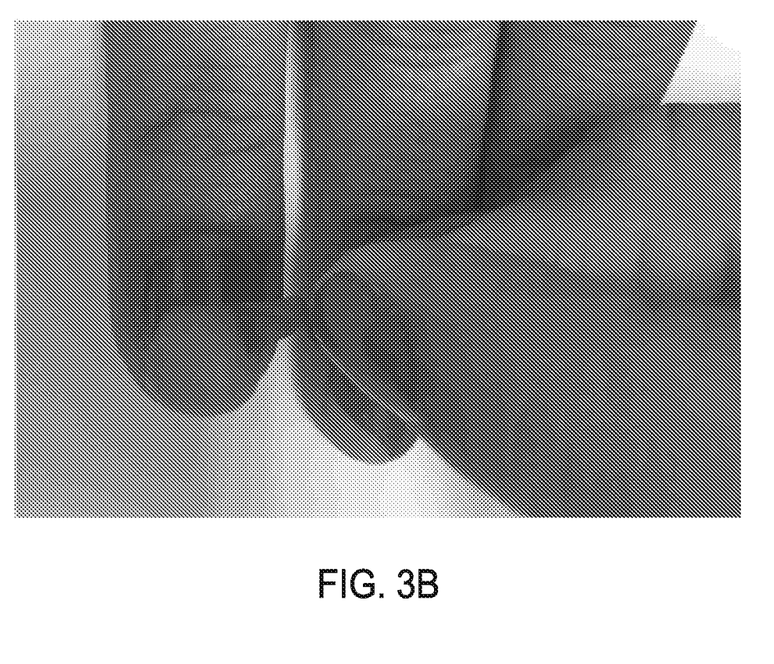

FIGS. 2A-B illustrate photographs of attempted peeling of a cured coating formed from 90 wt % Daitosol 3000 SLPN PE-1 and 10 wt % Avalure UR 450. FIGS. 3A-B illustrate photographs of attempted peeling of a cured coating, after 3 days wear, formed from Sample 1 (FIG. 3A) and Sample 2 (FIG. 3B), illustrating that the coating is monolithically peelable (e.g., in a continuous film). Although Sample 2 formed a harder film, it still peeled in a continuous film.

Example 3

Consumer study of Samples 1 and 2

A consumer study was undertaken using Samples 1 and 2 from Example 1. A three-week consumer study was conducted with 28 panelists to evaluate the invention as a water-based nail treatment. Panelist performance ratings were high when the product was initially applied. Panelists were instructed to peel and reapply the base coat daily as needed. Performance ratings were high, suggesting that the sealant base coat helps protect the nail from chipping, splitting, cracking and peeling.

The terms and expressions that have been employed are used as terms of description and not of limitation, and there is no intention in the use of such terms and expressions of excluding any equivalents of the features shown and described or portions thereof, but it is recognized that various modifications are possible within the scope of the embodiments of the present invention. Thus, it should be understood that although the present invention has been specifically disclosed by specific embodiments and optional features, modification and variation of the concepts herein disclosed may be resorted to by those of ordinary skill in the art, and that such modifications and variations are considered to be within the scope of embodiments of the present invention.

Enumerated Embodiments

The following exemplary embodiments are provided, the numbering of which is not to be construed as designating levels of importance:

Embodiment 1 provides a water-based nail-treatment composition comprising:

a first film-forming copolymer that is a copolymer of a ($C_1$-$C_5$)alkyl ester of methacrylic acid, of a ($C_1$-$C_5$)alkyl ester of acrylic acid, or a combination thereof, and of methacrylic acid; and a second film-forming copolymer that is a copolymer of isophorone diisocyanate, a poly(($C_2$-$C_3$)alkylene oxide), and 2,2-bis(methylol)propionic acid.

Embodiment 2 provides the nail-treatment composition of Embodiment 1, wherein the first film-forming copolymer is about 5 wt % to about 90 wt % of the nail-treatment composition.

Embodiment 3 provides the nail-treatment composition of any one of Embodiments 1-2, wherein the first film-forming copolymer is about 40 wt % to about 55 wt % of the nail-treatment composition.

Embodiment 4 provides the nail-treatment composition of any one of Embodiments 1-3, wherein the first film-forming copolymer is a copolymer of methacrylic acid, butyl acrylate, and methyl methacrylate.

Embodiment 5 provides the nail-treatment composition of any one of Embodiments 1-4, wherein the second film-forming copolymer is about 1 wt % to about 95 wt % of the nail-treatment composition.

Embodiment 6 provides the nail-treatment composition of any one of Embodiments 1-5, wherein the second film-forming copolymer is about 5 wt % to about 20 wt % of the nail-treatment composition.

Embodiment 7 provides the nail-treatment composition of any one of Embodiments 1-6, wherein the polyoxy($C_2$-$C_3$) alkylene is a poly(propylene oxide).

Embodiment 8 provides the nail-treatment composition of any one of Embodiments 1-7, wherein the polyoxy($C_2$-$C_3$) alkylene is a poly(propylene oxide) having a degree of polymerization of about 17.

Embodiment 9 provides the nail-treatment composition of any one of Embodiments 1-8, wherein the second film-forming copolymer is a copolymer is polypropylene glycol-17, isophorone diisocyanate, and 2,2-bis(methylol)propionic acid.

Embodiment 10 provides the nail-treatment composition of any one of Embodiments 1-9, further comprising a thickener.

Embodiment 11 provides the nail-treatment composition of Embodiment 10, wherein the thickener is a copolymer of steareth-20 methacrylate and one or more of acrylic acid and of methacrylic acid or a ($C_1$-$C_5$)alkyl ester thereof, wherein the copolymer is crosslinked with an allyl ether of pentaerythritol, an allyl ether of trimethylolpropane, or a combination thereof.

Embodiment 12 provides the nail-treatment composition of any one of Embodiments 10-11, wherein the thickener is about 0.001 wt % to about 10 wt % of the nail-treatment composition.

Embodiment 13 provides the nail-treatment composition of any one of Embodiments 10-12, wherein the thickener is about 0.05 wt % to about 2 wt %.

Embodiment 14 provides the nail-treatment composition of any one of Embodiments 1-13, wherein water is about 10 wt % to about 95 wt % of the nail-treatment composition.

Embodiment 15 provides the nail-treatment composition of any one of Embodiments 1-14, wherein water is about 50 wt % to about 70 wt % of the nail-treatment composition.

Embodiment 16 provides the nail-treatment composition of any one of Embodiments 1-15, further comprising a biomimetic composition comprising an oil-based portion and optionally a water-based portion.

Embodiment 17 provides the nail-treatment composition of Embodiment 16, wherein the biomimetic composition is about 0.001 wt % to about 50 wt % of the nail-treatment composition.

Embodiment 18 provides the nail-treatment composition of any one of Embodiments 16-17, wherein the oil-based portion is about 0.01 wt % to about 100 wt % of the biomimetic composition.

Embodiment 19 provides the nail-treatment composition of any one of Embodiments 16-18, wherein the oil-based portion comprises one or more natural oils.

Embodiment 20 provides the nail-treatment composition of any one of.

Embodiments 16-19, wherein the oil-based portion comprises abyssinian oil, coconut oil, and green coffee oil, or a combination thereof.

Embodiment 21 provides the nail-treatment composition of any one of Embodiments 16-20, wherein the water-based portion is about 0.01 wt % to about 99.99 wt % of the biomimetic composition.

Embodiment 22 provides the nail-treatment composition of any one of Embodiments 16-21, wherein the water-based portion comprises one or more natural extracts.

Embodiment 23 provides the nail-treatment composition of any one of Embodiments 16-22, wherein the water-based portion comprises garlic extract, horsetail extract, marshmallow extract, or a combination thereof.

Embodiment 24 provides the nail-treatment composition of any one of Embodiments 1-23, further comprising one or more colorants.

Embodiment 25 provides the nail-treatment composition of any one of Embodiments 1-24, wherein the nail-treatment composition is substantially free of colorants.

Embodiment 26 provides the nail-treatment composition of any one of Embodiments 1-25, wherein the nail-treatment composition is substantially free of nitrocellulose.

Embodiment 27 provides the nail-treatment composition of any one of Embodiments 1-26, wherein the nail-treatment composition is substantially free of nitrocellulose derivatives.

Embodiment 28 provides the nail-treatment composition of any one of Embodiments 1-27, wherein the nail-treatment composition is substantially free of volatile organic solvents.

Embodiment 29 provides the nail-treatment composition of any one of Embodiments 1-28, wherein the nail-treatment composition is substantially free of phthalates.

Embodiment 30 provides the nail-treatment composition of any one of Embodiments 1-29, wherein the nail-treatment composition is substantially free of plasticizers.

Embodiment 31 provides the nail-treatment composition of any one of

Embodiments 1-30, further comprising a defoamer, an adhesion promoter, a film-forming polymer, a photoinitiator, a filler, a rheology modifier, a thixotropic agent, a plasticizer, an oil, a UV absorber, a UV stabilizing agent, a surfactant, a dispersant, or a combination thereof.

Embodiment 32 provides the nail-treatment composition of any one of Embodiments 1-31, wherein the nail-treatment composition is a basecoat.

Embodiment 33 provides the nail-treatment composition of any one of Embodiments 1-32, wherein the nail-treatment composition is a topcoat.

Embodiment 34 provides the nail-treatment composition of any one of Embodiments 1-33, wherein the nail-treatment composition is an enamel.

Embodiment 35 provides the nail-treatment composition of any one of Embodiments 1-34, wherein a cured nail coating formed from the nail-treatment composition is monolithically peelable from the nail.

Embodiment 36 provides a cured product of the nail-treatment composition of any one of Embodiments 1-35.

Embodiment 37 provides a method of using the nail-treatment composition of any one of Embodiments 1-35, the method comprising:

applying the nail-treatment composition of any one of Embodiments 1-35 to a nail surface; and allowing the nail-treatment composition to cure on the nail surface to form a cured product of the nail-treatment composition.

Embodiment 38 provides the method of Embodiment 37, wherein the nail-treatment composition is applied directly to the nail surface without intervening layers.

Embodiment 39 provides the method of any one of Embodiments 37-38, wherein the nail-treatment composition is applied to one or more treatment layers on the nail surface.

Embodiment 40 provides the method of any one of Embodiments 37-39, further comprising applying to the cured product of the nail-treatment composition one or more additional nail-treatment compositions that are the same or different as the nail-treatment composition of any one of Embodiments 1-35.

Embodiment 41 provides a water-based nail-treatment composition comprising:

a first film-forming copolymer that is about 5 wt % to about 90 wt % of the nail treatment composition and that is a copolymer of methacrylic acid, butyl acrylate, and methyl methacrylate; and a second film-forming copolymer that is about 1 wt % to about 95 wt % of the nail-treatment composition and that is a copolymer of isophorone diisocyanate, polypropylene glycol-17, and 2,2-bis(methylol)propionic acid;

wherein the nail-treatment composition is substantially free of nitrocellulose, and a cured nail coating formed from the nail-treatment composition is monolithically peelable from the nail.

Embodiment 42 provides a nail-treatment composition comprising:

a biomimetic composition comprising an oil-based portion comprising two or more of green coffee oil, coconut oil, and Abyssinian oil, and optionally, a water-based portion comprising garlic extract, horsetail extract, marshmallow extract, or a combination thereof.

Embodiment 43 provides the nail-treatment composition of any one of Embodiments 1-34, wherein the nail-treatment composition further comprises a coalescing agent chosen from glycerol ethers, glycerol ether esters, ester alcohols, branched or linear $(C_1\text{-}C_6)$alkyl acetates, or combinations thereof.

Embodiment 44 provides the nail-treatment composition of Embodiment 43, wherein the coalescing agent comprises less than 5 wt % of a $(C_1\text{-}C_6)$alkyl acetate.

Embodiment 45 provides the nail-treatment composition of Embodiments 43-44, wherein the coalescing agent is butyl acetate, and the butyl acetate is less than about 5 wt % of the nail-treatment composition.

Embodiment 46 provides a cured product of the nail-treatment composition of Embodiments 43-45.

Embodiment 47 provides the cured product of Embodiment 46, wherein the cured product is a long wear cured coating.

Embodiment 48 provides the composition, cured product thereof, or method of any one or any combination of Embodiments 1-47 optionally configured such that all elements or options recited are available to use or select from.

What is claimed is:

1. A water-based nail-treatment composition comprising:
a water solvent in a range of about 10 wt % to 95 wt % of the nail-treatment composition;
a coalescing agent that is less than 5 wt % of the nail-treatment composition, the coalescing agent comprising a glycerol ether, a glycerol ether ester, an ester alcohol, a branched or linear ($C_1$-$C_6$)alkyl acetate, or a mixture thereof;

a first film-forming copolymer that is a copolymer of a ($C_1$-$C_5$)alkyl ester of methacrylic acid, of a ($C_1$-$C_5$) alkyl ester of acrylic acid, or a combination thereof, and of methacrylic acid;

a second film-forming copolymer that is a copolymer of isophorone diisocyanate, a poly(($C_2$-$C_3$)alkylene oxide), and 2,2-bis(methylol)propionic acid; and a biomimetic composition in a range of from 0.001 wt % to 50 wt % of the composition, the biomimetic composition comprising:
an oil-based portion comprising two or more of green coffee oil, coconut oil, and Abyssinian oil, and
a water-based portion comprising garlic extract, horsetail extract, or a combination thereof.

2. The nail-treatment composition of claim 1, wherein the first film-forming copolymer is about 5 wt % to about 90 wt % of the nail-treatment composition.

3. The nail-treatment composition of claim 1, wherein the first film-forming copolymer is about 40 wt % to about 55 wt % of the nail-treatment composition.

4. The nail-treatment composition of claim 1, wherein the first film-forming copolymer is a copolymer of methacrylic acid, butyl acrylate, and methyl methacrylate.

5. The nail-treatment composition of claim 1, wherein the second film-forming copolymer is about 1 wt % to about 95 wt % of the nail-treatment composition.

6. The nail-treatment composition of claim 1, wherein the second film-forming copolymer is about 10 wt % to about 20 wt % of the nail-treatment composition.

7. The nail-treatment composition of claim 1, wherein the second film-forming copolymer is a copolymer is polypropylene glycol, isophorone diisocyanate, and 2,2-bis(methylol)propionic acid.

8. The nail-treatment composition of claim 1, further comprising a thickener.

9. The nail-treatment composition of claim 8, wherein the thickener is about 0.001 wt % to about 10 wt % of the nail-treatment composition.

10. The nail-treatment composition of claim 1, wherein water is about 50 wt % to about 70 wt % of the nail-treatment composition.

11. The nail-treatment composition of claim 1, further comprising a biomimetic composition comprising
the oil-based portion is in a range of 0.01 wt % to 99.9 wt % of the biomimetic composition, and
the water-based portion is in a range of 0.01 wt % to 99.9 wt % of the biomimetic composition.

12. The nail-treatment composition of claim 1, further comprising one or more colorants.

13. A cured product of the nail-treatment composition of claim 1.

14. The cured product of claim 13, wherein the cured product is a long wear and peelable cured coating.

15. The cured product of claim 13, wherein the cured product is a long wear cured coating.

16. The cured product of claim 15, wherein the coalescing agent is butyl acetate, and the butyl acetate is less than about 2 wt % of the nail-treatment composition.

17. A method of using a nail-treatment composition, the method comprising:
applying a nail-treatment composition to a nail surface, the nail-treatment composition comprising
a water solvent in a range of about 10 wt % to 95 wt % of the nail-treatment composition;
a coalescing agent that is less than 5 wt % of the nail-treatment composition, the coalescing agent comprising a glycerol ether, a glycerol ether ester, an ester alcohol, a branched or linear ($C_1$-$C_6$)alkyl acetate, or a mixture thereof;
a first film-forming copolymer that is a copolymer of a ($C_1$-$C_5$)alkyl ester of methacrylic acid, of a ($C_1$-$C_5$) alkyl ester of acrylic acid, or a combination thereof, and of methacrylic acid, and
a second film-forming copolymer that is a copolymer of isophorone diisocyanate, a poly(($C_2$-$C_3$)alkylene oxide), and 2,2-bis(methylol)propionic acid;
a biomimetic composition in a range of from 0.001 wt % to 50 wt % of the composition, the biomimetic composition comprising:
an oil-based portion comprising two or more of green coffee oil, coconut oil, and Abyssinian oil, and
a water-based portion comprising garlic extract, horsetail extract, or a combination thereof; and
allowing the nail-treatment composition to cure on the nail surface to form a cured product of the nail-treatment composition.

18. The method of claim 17, wherein the nail-treatment composition is applied directly to the nail surface without intervening layers.

19. The method of claim 17, wherein the nail-treatment composition is applied to one or more treatment layers on the nail surface.

20. A nail-treatment composition comprising:
a biomimetic composition in a range of from 0.001 wt % to 50 wt % of the composition, the biomimetic composition comprising
an oil-based portion in a range of 0.01 wt % to 99.9 wt % of the biomimetic composition and comprising two or more of green coffee oil, coconut oil, and Abyssinian oil, and
a water-based portion in a range of 0.01 wt % to 99.9 wt % of the biomimetic composition and comprising garlic extract, horsetail extract, or a combination thereof and further comprising a water solvent in a range of about 10 wt % to 95 wt % of the nail-treatment composition and a coalescing agent that is less than 5 wt % of the nail-treatment composition, the coalescing agent comprising a glycerol ether, a glycerol ether ester, an ester alcohol, a branched or linear ($C_1$-$C_6$)alkyl acetate, or a mixture thereof.

* * * * *